United States Patent [19]

Eberle et al.

[11] Patent Number: 4,766,107
[45] Date of Patent: Aug. 23, 1988

[54] 16-OXA-BICYCLO-[13.1.0]-HEXADEC-7-ENE AND ITS APPLICATION AS A FRAGRANCE

[75] Inventors: Hans-Jürgen Eberle; Helmut Gebauer, both of Munich, Fed. Rep. of Germany

[73] Assignee: Consortium fur Elektrochemische Industrie GmbH, Munich, Fed. Rep. of Germany

[21] Appl. No.: 855,350

[22] Filed: Apr. 24, 1986

[30] Foreign Application Priority Data

Aug. 29, 1985 [DE] Fed. Rep. of Germany ....... 3530885

[51] Int. Cl.⁴ ..................... A61K 7/46; C07D 303/04
[52] U.S. Cl. ........................................ 512/13; 549/546
[58] Field of Search ................ 549/546; 252/522; 512/13

[56] References Cited

U.S. PATENT DOCUMENTS 3,845,078 10/1974 Lemberg .............................. 549/546
4,668,836 5/1987 Eberle et al. ......................... 585/364

FOREIGN PATENT DOCUMENTS 1479165 3/1967 France ................................ 549/546
111195 2/1975 German Democratic Rep. .

OTHER PUBLICATIONS

Journal für praktische Chemie, 323, 177–187 (1981).
Dale et al., J. Chem. Soc., 73–86 (1963).

*Primary Examiner*—Norma S. Milestone
*Attorney, Agent, or Firm*—Collard, Roe & Galgano

[57] ABSTRACT

The compound 16-oxa-bicyclo-[13.1.0]-hexadec-7-ene, and a process for its production, having the structural formula:

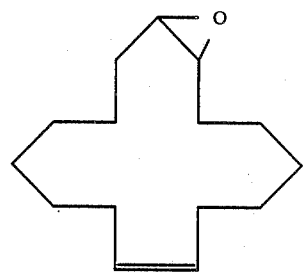

is disclosed. 16-oxa-bicyclo-[13.1.0]-hexadec-7-ene is useful as a fragrance and may be produced by reacting cyclopentadeca-1,8-diene in the presence of an organic peracid.

3 Claims, No Drawings

16-OXA-BICYCLO-[13.1.0]-HEXADEC-7-ENE AND ITS APPLICATION AS A FRAGRANCE

The present invention relates to a compound 16-oxa-bicyclo-[13.1.0]-hexadec-7-ene, and its use in a fragrance composition. The compound of this present invention may be represented by the structural formula:

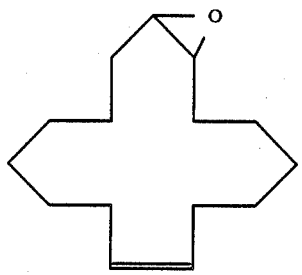

The compound according to the invention is obtainable by the partial oxidation of cyclopentadeca-1,8-diene with peracids.

A process for producing 16-oxa-bicyclo-[13.1.0]-hexadec-7-ene includes the step of reacting cyclopentadeca-1,8-diene in the presence of organic peracids.

Examples of some suitable peracids that can be used, according to the invention, are performic acid, peracetic acid, m-chloroperbenzoic acid, among other acids. The preparation or in situ preparation of the peroxocompounds is by methods currently known to the art.

The initial product, cyclopentadeca-1,8-diene, is a compound known to the skilled art worker. The compound is obtainable, for example, by cometathesis of cyclooctene and cycloheptene on metathesis catalysts, such as, for example, rhenium heptoxide.

Cyclopentadeca-1,8-diene and peracid are reacted in approximately equimolar amounts. As a general rule, the molar ratio of diene to peracid amounts is 1:0.7 to 1.1; in particular, 1:0.8 to 1.

Generally, the process is carried out in the inert solvents, such as methylene chloride, chloroform, carbon tetrachloride, dichloroethane, and others; however, the presence of such solvents is not an absolute requirement.

In order to suppress epoxidizing of the second olefin bond, the diene is advantageously charged first and the peracid subsequently added by dosing.

The compound according to the present invention is useful as a fragrance. It offers a fragrance profile or picture dominated by warm and sensual notes, combining in a harmonious way amber, musk and woody notes. Additionally, the fragrance according to the invention has very good properties of tenacity and fixation. The fragrance can be used, for example, for scenting cosmetic and technical products and, owing to the high quality of its scent, is particularly suitable for use as a fixative and basic note in the production of fine perfumes.

Moreover, the compound of the present invention may be used as the initial substance in the synthesis of the ketones cyclopentadec-7-ene-1-one and cyclopentadec-8-ene-1-on, which, in turn, are useful as fragrances. The epoxide may be reacted to the corresponding ketone by known methods, for example by treating the epoxide with acids or Lewis acids.

The invention will now be more fully described by the following examples. It should, however, be noted that such examples are given by way of illustration and not of limitation.

EXAMPLE 1

Preparation of 16-oxa-bicyclo-[13.1.0]-hexadec-7-ene

To a mixture consisting of 100 g (0.49 moles) cyclopentadeca-1,8-diene, 217 g (1.6 moles) sodium acetate$\times 3$ $H_2O$ and 1000 ml methylene chloride, 78 ml 40% by wt. (0.47 moles) peracetic acid is added dropwise within 2 hours under stirring. The reaction temperature is 2° C. Subsequently, stirring is continued for another 30 minutes at the same temperature and the mixture is subsequently heated to room temperature. After another 2 hours of stirring at room temperature, the reaction mixture is washed first with $5\times 100$ ml water, subsequently with 100 ml 5% by wt. sodium bicarbonate solution, and finally with 100 ml saturated sodium chloride solution and thus rendered neutral and free from peroxide. Subsequently, the phases are separated. The organic phase is dried over sodium sulfate. After removing the solvent, the product mixture is subjected to fractional distillation. 53 grams of the desired product is obtained in additon to 35 g initial substance (cyclopentadeca-1,8-diene) and 11 g cyclopentadecadiene dioxide.

The desired product is characterized by the following data:

Boiling point at 0.013 mbar: 100° C.

Mass spectrum: m/e (intensity, %) 222 (I, molecule ion), 204 (0.4) 165 (7), 147 (7), 121 (15), 109 (25), 95 (41), 81 (60), 67 (95), 41 (100).

EXAMPLE 2

Application of 16-oxa-bicyclo-[13.1.0]-hexadec-7-ene as fragrance; florid fantasy composition:

|  | a | b |
| --- | --- | --- |
| Synambran 1% in DPG (tetramethylperhydronaphthofurane) | 40 | 40 |
| Dihydromyrcenol | 60 | 60 |
| Orange oil bras. | 60 | 60 |
| Nerolialdehyde (2,5-dimethyl-2-vinyl-4-hexenal) | 20 | 20 |
| Lavender oil Barreme | 60 | 60 |
| Benzylacetate | 60 | 60 |
| Hexylzimtaldehyde alpha | 140 | 140 |
| Jaswalia (4-acetoxy-3-pentyl-2H—tetrahydropyrane) | 80 | 80 |
| Methylionone gamma | 60 | 60 |
| Phenyl ethanol | 110 | 110 |
| Carnation oil, Sanzibar | 15 | 15 |
| Benzylsalicylate | 45 | 45 |
| Lignoxan (14-methyl-13-oxa-bicyclo-(10,3,0)-pentadecane) | 30 | 30 |
| Galbanum oil 10% in DPG | 30 | 30 |
| Sandalwood Oil | 40 | 40 |
| Dipropylene glycol | 60 | — |
| 16-oxa-bicyclo-[13.1.0]hexadec-7-ene | — | 60 |
|  | 1000 | 1000 |

Composition a is a florid fantasy composition. A perfume oil with a warm, natural musk note with pronounced woody and ambered aspects is obtained by adding 60 parts by weight of the compound according to the present invention. The profile of the overall scent is finer and rounded, or more balanced.

While only several embodiments and examples of the present invention have been described, it is obvious that many changes and modifications may be made thereunto, without departing from the spirit and scope of the invention.

What is claimed is:

1. 16-oxo-bicyclo-[13.1.0]-hexadec-7-ene having the structural formula:

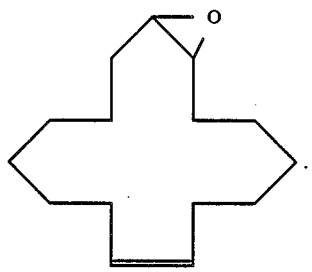

2. A composition for use as a fragrance, comprising 16-oxa-bicyclo-[13.1.0]-hexadec-7-ene having the structural formula:

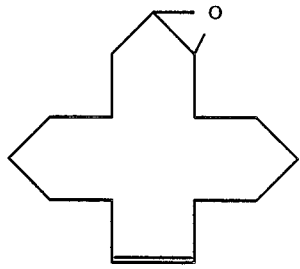

3. The composition according to claim 2, wherein 16-oxa-bicyclo-[13.1.0]-hexadec-7-ene is approximately 6%, by weight, of said composition.

* * * * *